US009307941B2

(12) United States Patent
Johansson et al.

(10) Patent No.: US 9,307,941 B2
(45) Date of Patent: Apr. 12, 2016

(54) PATIENT MANAGEMENT DEVICE, SYSTEM AND METHOD

(71) Applicant: Bläckbild, Ängelholm (SE)

(72) Inventors: Per Johansson, Ängelholm (SE); Sture Karlander, Ängelholm (SE); Patrik Jönsson, Munka Ljungby (SE); Jan Boberg, Ängelholm (SE)

(73) Assignee: Bläckbild, Ängelholm (SE)

( * ) Notice: Subject to any disclaimer, the term of this patent is extended or adjusted under 35 U.S.C. 154(b) by 0 days.

(21) Appl. No.: 14/447,474

(22) Filed: Jul. 30, 2014

(65) Prior Publication Data

US 2015/0190084 A1    Jul. 9, 2015

Related U.S. Application Data

(62) Division of application No. 12/994,440, filed as application No. PCT/EP2009/056689 on May 29, 2009, now Pat. No. 8,821,416.

(60) Provisional application No. 61/159,908, filed on Mar. 13, 2009.

(30) Foreign Application Priority Data

May 29, 2008 (SE) ........................................ 0801267

(51) Int. Cl.
*A61B 5/103*    (2006.01)
*A61B 5/117*    (2006.01)
(Continued)

(52) U.S. Cl.
CPC ............... *A61B 5/222* (2013.01); *A61B 5/0022* (2013.01); *A61B 5/0024* (2013.01);
(Continued)

(58) Field of Classification Search
CPC .......................................................... A61B 5/00
USPC ................................................... 600/587, 595
See application file for complete search history.

(56) References Cited

U.S. PATENT DOCUMENTS 4,353,375 A    10/1982  Colburn et al.
5,197,489 A *  3/1993   Conlan ......................... 600/595
(Continued)

FOREIGN PATENT DOCUMENTS

EP    0972489 A2       1/2000
WO    WO00/47108 A1    8/2000
WO    WO2006/088415 A1 8/2006

OTHER PUBLICATIONS

United States Patent and Trademark Office, Notice of Allowance mailed Apr. 29, 2014 in U.S. Appl. No. 12/994,440, 10 pages.
(Continued)

*Primary Examiner* — Rene Towa
*Assistant Examiner* — May Abouelela
(74) *Attorney, Agent, or Firm* — Inskeep IP Group, Inc.

(57) ABSTRACT

A portable apparatus for managing a plurality of events related to a patient and for recording and storing input data related to said events is disclosed. The portable apparatus comprises a man machine user interface; a timer unit; a control unit, arranged to provide an invitation to the patient as an instruction via the interface to perform a motion exercise, upon a trigger from the timer unit or upon a patient self initiation. In an embodiment the apparatus comprises a sensor to record measurements related to said motion exercise. Further, a storage unit is arranged to retrievably store patient input data and said measurements. This enables diagnosing a degree of a neurological disease or an effect of a medication on said neurological disease.

19 Claims, 6 Drawing Sheets

(51) Int. Cl.

| | | |
|---|---|---|
| *A61B 5/22* | (2006.01) | |
| *A61B 5/11* | (2006.01) | |
| *A61B 5/16* | (2006.01) | |
| *A61B 5/00* | (2006.01) | |
| *G06F 19/00* | (2011.01) | |
| *G06Q 50/22* | (2012.01) | |
| *A61B 5/0205* | (2006.01) | |
| *A61B 5/021* | (2006.01) | |

(52) U.S. Cl.
CPC ............ *A61B 5/0205* (2013.01); *A61B 5/1101* (2013.01); *A61B 5/1107* (2013.01); *A61B 5/1122* (2013.01); *A61B 5/1124* (2013.01); *A61B 5/16* (2013.01); *A61B 5/4082* (2013.01); *A61B 5/4519* (2013.01); *A61B 5/486* (2013.01); *A61B 5/4848* (2013.01); *A61B 5/681* (2013.01); *A61B 5/7278* (2013.01); *A61B 5/7285* (2013.01); *A61B 5/741* (2013.01); *A61B 5/7455* (2013.01); *A61B 5/7475* (2013.01); *G06F 19/3406* (2013.01); *G06F 19/3456* (2013.01); *G06F 19/3481* (2013.01); *G06F 19/363* (2013.01); *G06Q 50/22* (2013.01); *A61B 5/0002* (2013.01); *A61B 5/021* (2013.01); *A61B 2503/08* (2013.01); *A61B 2505/07* (2013.01); *A61B 2562/0219* (2013.01)

(56) References Cited

U.S. PATENT DOCUMENTS

| | | | | |
|---|---|---|---|---|
| 5,265,619 | A * | 11/1993 | Comby et al. | 600/595 |
| 5,293,879 | A * | 3/1994 | Vonk et al. | 600/595 |
| 5,562,104 | A * | 10/1996 | Hochberg et al. | 600/595 |
| 5,572,421 | A * | 11/1996 | Altman et al. | 705/3 |
| 5,573,013 | A * | 11/1996 | Conlan | 600/595 |
| 5,575,294 | A * | 11/1996 | Perry et al. | 600/587 |
| 5,772,611 | A | 6/1998 | Hocherman | |
| 5,885,231 | A | 3/1999 | Cramer et al. | |
| 6,022,315 | A * | 2/2000 | Iliff | 600/300 |
| 6,108,665 | A * | 8/2000 | Bair et al. | |
| 6,267,733 | B1 | 7/2001 | Peterson et al. | |
| 6,416,485 | B1 | 7/2002 | Rovetta et al. | |
| 6,561,992 | B1 | 5/2003 | Eberhart et al. | |
| 6,613,000 | B1 | 9/2003 | Reinkensmeyer et al. | |
| 7,455,648 | B2 | 11/2008 | Kandori et al. | |
| 7,708,699 | B2 | 5/2010 | Turner et al. | |
| 7,720,306 | B2 | 5/2010 | Gardiner et al. | |
| 7,725,175 | B2 | 5/2010 | Koeneman et al. | |
| 7,931,604 | B2 | 4/2011 | Even Zohar et al. | |
| 8,021,312 | B2 | 9/2011 | Kinnunem et al. | |
| 8,092,398 | B2 * | 1/2012 | Weinberg et al. | 600/595 |
| 8,187,209 | B1 | 5/2012 | Giuffrida | |
| 8,273,036 | B2 * | 9/2012 | Fong | 600/595 |
| 8,343,065 | B2 * | 1/2013 | Bartol et al. | 600/554 |
| 8,348,862 | B2 * | 1/2013 | Chu | 600/587 |
| 2002/0035486 | A1 | 3/2002 | Huyn et al. | |
| 2003/0208454 | A1 | 11/2003 | Rienhoff, Jr. et al. | |
| 2003/0216671 | A1 * | 11/2003 | Saruwarati et al. | 600/595 |
| 2004/0082979 | A1 * | 4/2004 | Tong et al. | 607/48 |
| 2004/0181115 | A1 | 9/2004 | Sandyk et al. | |
| 2005/0137134 | A1 | 6/2005 | Gill et al. | |
| 2005/0240086 | A1 * | 10/2005 | Akay | 600/300 |
| 2005/0240253 | A1 | 10/2005 | Tyler et al. | |
| 2006/0015153 | A1 * | 1/2006 | Gliner et al. | 607/45 |
| 2006/0252999 | A1 * | 11/2006 | Devaul et al. | 600/300 |
| 2006/0264786 | A1 * | 11/2006 | Nashner | 600/595 |
| 2006/0270949 | A1 | 11/2006 | Mathie et al. | |
| 2006/0276727 | A1 * | 12/2006 | Terrio | 600/595 |
| 2006/0287614 | A1 * | 12/2006 | Hogan et al. | 600/595 |
| 2007/0021689 | A1 | 1/2007 | Stergiou et al. | |
| 2007/0027369 | A1 | 2/2007 | Pagnacco et al. | |
| 2007/0112287 | A1 | 5/2007 | Fancourt et al. | |
| 2007/0118054 | A1 | 5/2007 | Pinhas et al. | |
| 2007/0249968 | A1 | 10/2007 | Miesel et al. | |
| 2007/0259717 | A1 * | 11/2007 | Mattice et al. | 463/36 |
| 2008/0001735 | A1 * | 1/2008 | Tran | 340/539.22 |
| 2008/0009772 | A1 | 1/2008 | Tyler et al. | |
| 2008/0096726 | A1 * | 4/2008 | Riley et al. | 482/8 |
| 2008/0221487 | A1 | 9/2008 | Zohar et al. | |
| 2008/0248871 | A1 | 10/2008 | Szturm et al. | |
| 2008/0262373 | A1 | 10/2008 | Burns et al. | |
| 2008/0287821 | A1 | 11/2008 | Jung et al. | |
| 2009/0060287 | A1 * | 3/2009 | Hyde et al. | 382/118 |
| 2009/0082701 | A1 | 3/2009 | Zohar et al. | |
| 2009/0192418 | A1 | 7/2009 | Miyashita et al. | |
| 2009/0247910 | A1 | 10/2009 | Klapper | |
| 2009/0264789 | A1 | 10/2009 | Molonar et al. | |
| 2009/0299232 | A1 * | 12/2009 | Lanfermann et al. | 600/595 |
| 2009/0318779 | A1 * | 12/2009 | Tran | 600/301 |
| 2009/0326419 | A1 | 12/2009 | Gonzalez Rojas et al. | |
| 2010/0049095 | A1 | 2/2010 | Bunn et al. | |
| 2010/0063116 | A1 | 3/2010 | Huth et al. | |
| 2010/0174586 | A1 * | 7/2010 | Berg et al. | 705/10 |
| 2010/0222179 | A1 * | 9/2010 | Temple et al. | 482/8 |
| 2011/0040204 | A1 * | 2/2011 | Ivorra et al. | 600/557 |
| 2011/0111014 | A1 | 5/2011 | Langston | |
| 2011/0245633 | A1 * | 10/2011 | Goldberg et al. | 600/301 |
| 2011/0245798 | A1 | 10/2011 | Gill et al. | |
| 2011/0313261 | A1 | 12/2011 | Bourget et al. | |
| 2012/0130286 | A1 | 5/2012 | Miesel et al. | |

OTHER PUBLICATIONS

United States Patent and Trademark Office, Final Office Action mailed Jul. 29, 2013 in U.S. Appl. No. 12/994,440, 12 pages.

United States Patent and Trademark Office, Office Action mailed Apr. 9, 2013 in U.S. Appl. No. 12/994,440, 14 pages.

WIPO, International Preliminary Examining Authority (European Patent Office), International Preliminary Report on Patentability mailed Sep. 6, 2010 in International Patent Application No. PCT/EP2009/056689, 11 pages.

WIPO, European International Search Authority, International Search Report and Written Opinion mailed Sep. 17, 2009 in International Patent Application No. PCT/EP09/56689, 4 pages.

Van Someren, E.J.W., "Actigraphic Monitoring of Movement and Rest-Activity Rhythms in Aging, Alzheimer's Disease, and Parkinson's Disease," *IEEE Transactions on Rehabilitation Engineering*, vol. 5, No. 4, Dec. 1997, pp. 394-398.

* cited by examiner

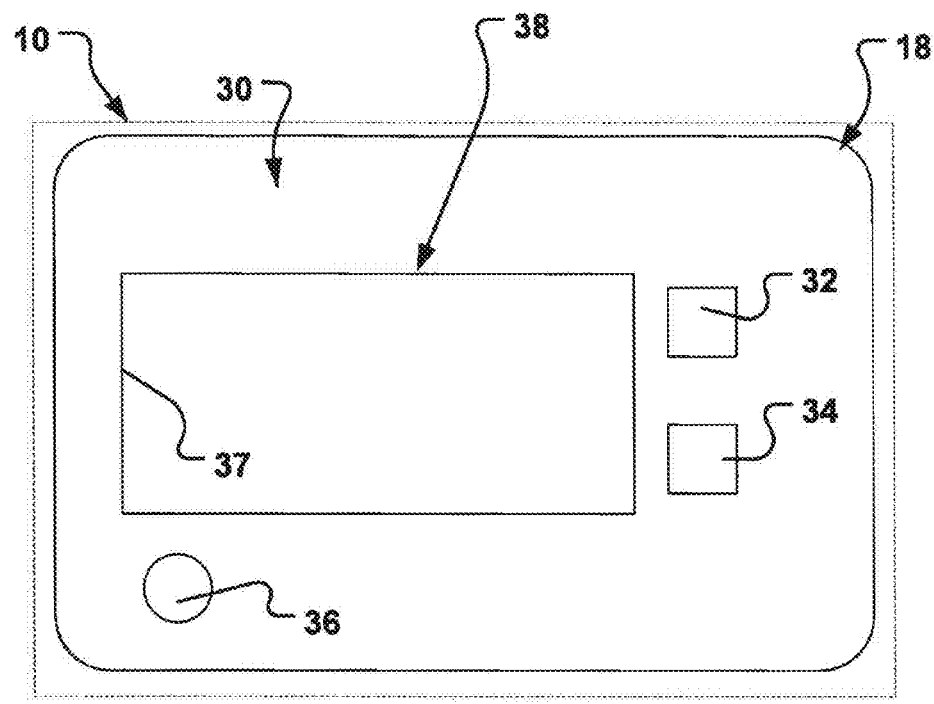
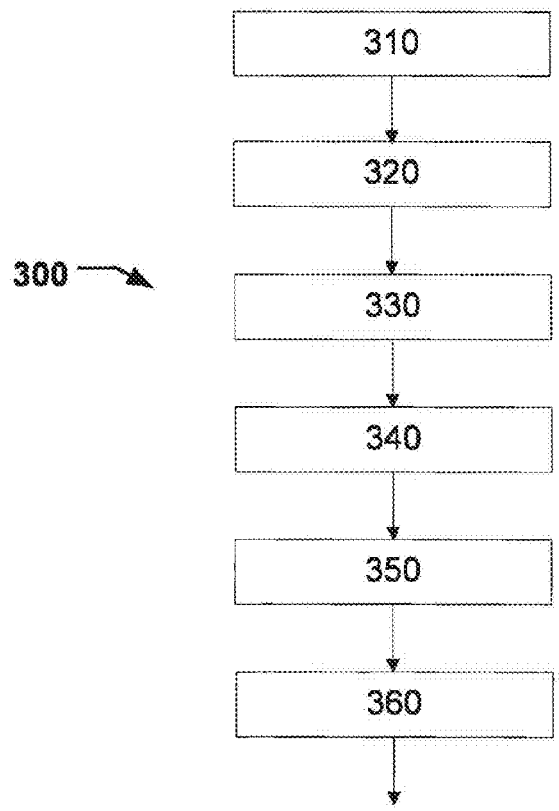
Fig. 2
Fig. 3

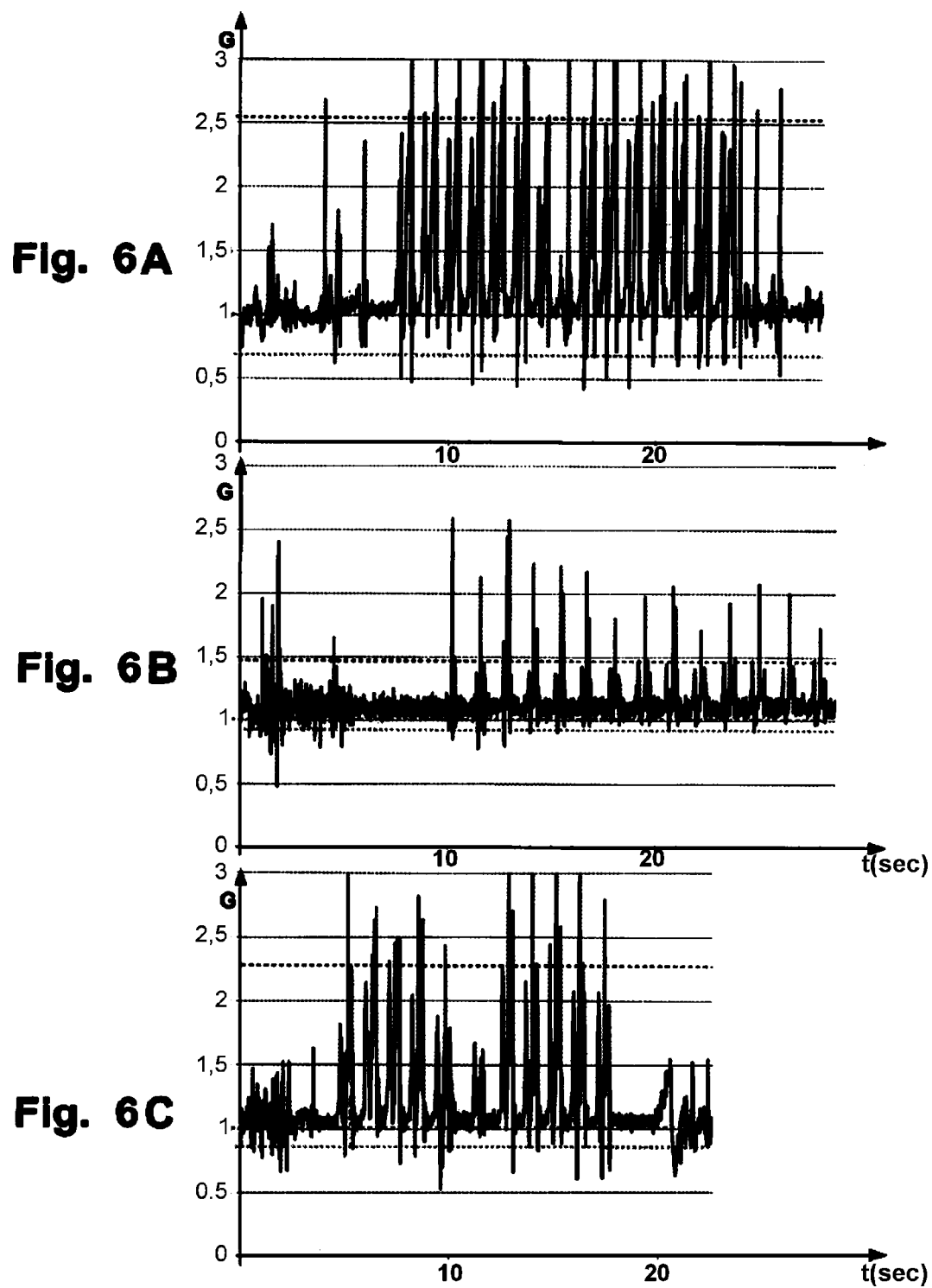

PATIENT MANAGEMENT DEVICE, SYSTEM AND METHOD

RELATED APPLICATIONS

This application is a divisional of U.S. patent application Ser. No. 12/994,440, Filing Date under 35 U.S.C. 371 Feb. 22, 2011, entitled Patient Management Device, System And Method, which is the U.S. National Stage of and claims priority to International Patent Application No. PCT/EP2009/056689, International Filing Date 29 May 2009, entitled Patient Management Device, System And Method, which claims priority to Swedish Patent Application No. SE0801267-6 filed 29 May 2008 entitled Metod För En Användarenhet, En Användarenhet Och Ett System Innefattande Nämnda Anvdarenhet; and U.S. Provisional Application Ser. No. 61/159,908 filed 13 Mar. 2009 entitled Patient Management Device and Method, all of which are hereby incorporated herein by reference in their entireties.

FIELD OF THE INVENTION

This invention pertains in general to the field of devices and methods for managing, including registering and/or triggering, of patient related occurrences or events. More particularly the invention relates to managing and surveillance of occurrences or events, and more particularly to managing occurrences or events which are time controlled or associated with or induced by medication and/or disease.

BACKGROUND OF THE INVENTION

Previously known management of diseases, such as chronic diseases, has various drawbacks. In traditional clinical surveillance of a patient who is suffering from a disease, such as chronic disease, and who spends most time as an outpatient, e.g. at home, the patient has a restricted number of meetings annually with a physician. These meetings usually take place in the clinic where the physician is based. During the meeting the development of the disease since the previous meeting is discussed between the patient and the physician for planning of continued therapy. At the best, the patient has made handwritten notes before the meeting at a regular or irregular basis. However, the notes are most often not read by the physician due of a lack of time needed to analyze the notes. Hence, while the physician often only is informed of the latest occurrences by the patient during the elapsed period, due to insufficient memory of the patient, many previous events are missed out and not considered by the physician. The patient has for instance simply forgotten these events, or forgotten to annotate the events, or wrongly annotated some events, or even annotated incorrect information related to such events. A common behavior is that patients do not want to trouble the doctor, and therefore withhold information from the doctor. Many patients do also not want to be sick, which has an influence on the disease related information given to the doctor.

Furthermore, while a patient gets prepared to meet a physician for such an appointment, the patient adopts intentionally or non-intentionally a recovered façade. By keeping up appearances, the patient shows a more healthy appearance towards the physician than the actual health condition actually is. Thus, the physician gets an inadequate physical and mental impression of the patient.

A consequence of the missed out information, following the physician's interpretation based on the visual impression of the patient status may be that substantial information that could affect the physician's judgment of the patient status is eluded. Thus, the subsequent advice and potential ordinations and amendments of prescriptions made by the physician may be substantially different from objective prescriptions. The patient may be advised to take a less effective dose, or a less effective type of medication, compared to when correct information was provided during the meeting between the patient and the physician.

For chronic patients, e.g. suffering from Parkinson's disease (PD), the above scenario is not uncommon and is an obstacle to overcome for the health providers, e.g. physicians responsible for correct treatment of the patient.

Electronic note keeping systems for collecting information such as above are an alternative. Known devices available on the market include handheld devices that may be used for storing information, including pocket pc's, mobile telephones, etc. However, these devices are difficult to handle for certain patients, in particular some elderly persons. In addition, due to extremely short life cycles before new models emerge, such devices are not suitable for long-term surveillance of a patient. For instance, costly adaptations of software or hardware have to be made in close intervals. Also, reliability of such devices is an issue, as frequent software updates and changes of hardware platform are not always a benefit for neither the patient nor the physician. Sequentially, as new hardware and new implementations are introduced, additional training is needed for personnel responsible at the health provider to secure adequate outcome of the monitoring and diagnosis.

In addition, commonly more obvious is the appearance especially concerning PD patients the presence of undesired motoric movement of some part of the body, e.g. a tremor of a limb such as an arm or a leg. These tremors occur because of an inadequate level of non-dopamine in the brain of the patient. However, only about 68% of the diagnosed PD patients suffer from such tremors and about half of these patients categorize these undesired movements as troublesome and/or embarrassing.

Systems to monitor and measure these tremors have been disclosed in e.g. EP0535508, or WO2008037260. These systems monitor and categorize the seriousness of the tremors in terms of momentarily measurements of motoric movements of a patient limb. However, the measurement outcome reflects the patient status at the specific time of measurement. More specifically, if anti-tremor medication prescribed by a physician, based on such measurements, the tremors are suppressed. The medication has to be taken in a certain dosage and in certain time intervals. However, when tremors are inhibited, the systems of e.g. EP0535508, or WO2008037260 provide no useful measurement values for a follow-up of the treatment. Hence, these systems are only beneficial tools for the physician and the patient suffering from undesired movements on a short term perspective. However, any approach to conjointly reduce or eliminate long term trends in the progression of the disease or treatment thereof is absent.

Hence, an improved patient friendly medical device and/or method, at least suitable for long-term monitoring, would be advantageous and in particular a portable apparatus allowing for increased flexibility, cost-effectiveness, easy handling in particular by a elderly patient population and/or user friendliness would be advantageous. There is a desire to provide such a device and/or method having high acceptance thanks to a low technical barrier experienced by the users when monitoring such patient population.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a device, a system, a method, a computer-readable medium, and a medical workstation, according to the appended patent claims.

According to a first aspect of the invention, a portable device is provided for managing a plurality of events related to a patient and for recording and storing input data related to the events. The portable apparatus comprises a man machine user interface comprising: an input unit for registering patient input data elements, and an output unit for providing information elements to the patient; a timer unit arranged to trigger at least a first event of the plurality of events and to tag the input data with a time stamp; the input unit being responsive to an invitation provided to the patient by the output unit and upon triggering the event, or being responsive to a patient self initiation; a control unit, arranged to provide the invitation as an instruction via the output unit to the patient to perform a motion exercise, upon the trigger from the timer unit or upon the patient self initiation; at least one sensor unit arranged to record measurement data elements related to the motion exercise of the patient; a storage unit, arranged to retrievably store the input data comprising the patient input data elements and the measurement data elements, when recorded by means of the input unit and/or the sensor unit, together with the time stamp, and wherein the storage unit is adapted to store the measurement data elements from the motion exercise performed upon the instruction or upon the patient self initiation of the motion exercise.

According to a second aspect of the invention, a system is provided that comprises in combination at least one apparatus according to the first aspect of the invention, and an external processing unit, wherein the storage unit is arranged to provide the stored input data for processing to the external processing unit, wherein the external processing unit and/or the control unit is adapted to derive diagnostic data from the stored measurement data elements; and wherein the external processing unit and/or the control unit is adapted to provide a long-term summarized report of the stored input data for a physician.

According to a third aspect of the invention, a method or system is provided for diagnosing a degree of a neurological disease or an effect of a medication on the neurological disease, the method (or the system) comprising (units for): registering movement of the portable apparatus by registration of an output signal from an accelerometer of a portable apparatus during a pre-defined motion exercise, and storing the output signal as measurement data elements, and analyzing the measurement data for determining the degree of a neurological disease or an effect of a medication on the neurological disease. A neurological disease is for instance Parkinson's Disease (PD). Another neurological disease is Multiple Sclerosis (MS). A further neurological disease is Stroke. When an accelerometer is used as described hereinafter, the neurological disease comprises diseases that imply impaired agility.

According to a further aspect of the invention, a computer program is provided. The computer program comprises code segments for out of the method according to the third aspect of the invention.

Further embodiments of the invention are defined in the dependent claims, wherein features for the second and subsequent aspects of the invention are as for the first aspect mutatis mutandis.

Some embodiments of the invention provide for an improved patient-doctor communication.

Some embodiments of the invention facilitate for the patient to provide information, and in particular disease-related information, to the doctor. Disease-related information comprises information such as concerning well-being of the patient, including states of pain, subjective sickness, etc; events related to a disease, like frequency and intensity of tumbling; medication intake—time or interval and dosage during a time period; etc.

Some embodiments of the invention also provide for a standardized format of reports of disease related information.

Some embodiments of the invention provide for registration of information at a point of time. The point of time may be the time at which the patient receives at least one question from the apparatus, wherein the time may be pre-determined, arbitrary, or chosen by the patient. The point of time may be the time of an event.

Some embodiments of the invention provide for registration of information by the patient at home, or in another non-clinical environment where the patient feels comfortable. In this manner, the surroundings or situation when entering information does not influence the recorded data in contrast to being in the aforementioned clinical environment.

Some embodiments of the invention provide for registration of information by the patient, wherein the subjective information of the patient is separated from objective information, or wherein the subjective information is removed from the objective information. The subjective information is dependent on memory and experience or conception of a patient, e.g. of an event. In objective information, this subjective information is not existent or removed. For a doctor, the objective information thus provided is very valuable for an assessment of a course of a disease and the seriousness of the disease, as well as determination of a therapy based thereon.

Some embodiments of the invention provide for objective measurement values. The objective measurement values are for instance a state of a disease, an effect or efficiency of an administered or taken medicine. The novel objective measurement values may be compared to, but differ from, measurement values based on blood samples, blood pressure measurements, or other monitored physiological functions of a patient.

Some embodiments of the invention provide for long-term registration, overview and follow-up of information from a patient.

Some embodiments provide for a measurement value for an effect of a medication on a disease, e.g. on a neurological disease, such as Parkinson's Disease. Thus, some embodiments provide for an adjustment of an active dose and/or time of administration of such a medication.

Some embodiments provide for measurement values related to a motor section of an Unified Parkinson's Disease Rating Scale (UPDRS).

Some embodiments of the invention provide for a dedicated hardware platform for long-term use over many years. Thus, a dependency of other mobile apparatus manufacturers and rapid evolvement of consumer models, such as mobile telephones, is advantageously avoided.

Some embodiments of the invention provide for a simple user interface suitable for use by elderly, or motory disabled patients.

The terms "occurrence" and "event" in the context of the present application is directed towards an actual instance in time where a specific situation arises or an incident arrives, happens or arises from a preceding state of things. An event may reoccur regularly or irregularly. An event may for instance be a tremor attack of a patient, a patient feeling sick, a patient tumbling, a patient having headache. On the other hand, an event may be time triggered. Time triggered events comprise an alarm set off, or an invitation by a device to a patient to enter desired data, make desired measurements, or perform a certain training element for a measurement.

The g-force (hereinafter called "G") on an object is its acceleration relative to free-fall. An acceleration of one G is equal to standard gravity, which is approximately 9.81 meters per square second. Some embodiments of portable apparatuses comprise sensors to measure g-force.

A specific application of the invention is related to managing patients suffering from movement disorders, such as Parkinson's disease (PD) or similar, and to record events associated with the pathological picture thereof. The following description focuses on an embodiment of the present invention applicable to situations experienced by a PD patient and in particular to an outpatient management and surveillance. However, it will be appreciated that the invention is not limited to this application but may be applied to many other situations, e.g. where the effect of or interaction with a pharmaceutical is of interest including for example studies related to monitoring an effect on a medication. Other fields of application may comprise rehabilitation, psychic diseases, pain management, etc. The portable apparatus provides a means of finding a degree of "well-being" of a patient. This well-being may be recorded or determined for a specific time of a day, or over a period of a day. It may also be diagnosed in a more long-term trend over weeks or months, before re-visiting a doctor. The more complicated it is to find a medication that is correct or convenient for a patient, the more advantageous is the use of embodiments of the portable apparatus.

A time stamp includes both date and time at that date. A time stamp may be provided in form of a sequence of characters, or it may be based on another consistent data format suitable for processing. The time stamp allows for logging of events. A plurality of time stamps, each of which is related to a specific event, allows for various operations like comparison, or tracking progress.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 2 is a schematic illustration of an implementation of the portable device;

FIG. 3 is a flow chart of an embodiment of a method implemented by means of the portable device;

FIGS. 4A-C, 5A-C, and 6A-C are graphs of measurement curves made by means of the portable device.

DESCRIPTION OF EMBODIMENTS

Figure 1:
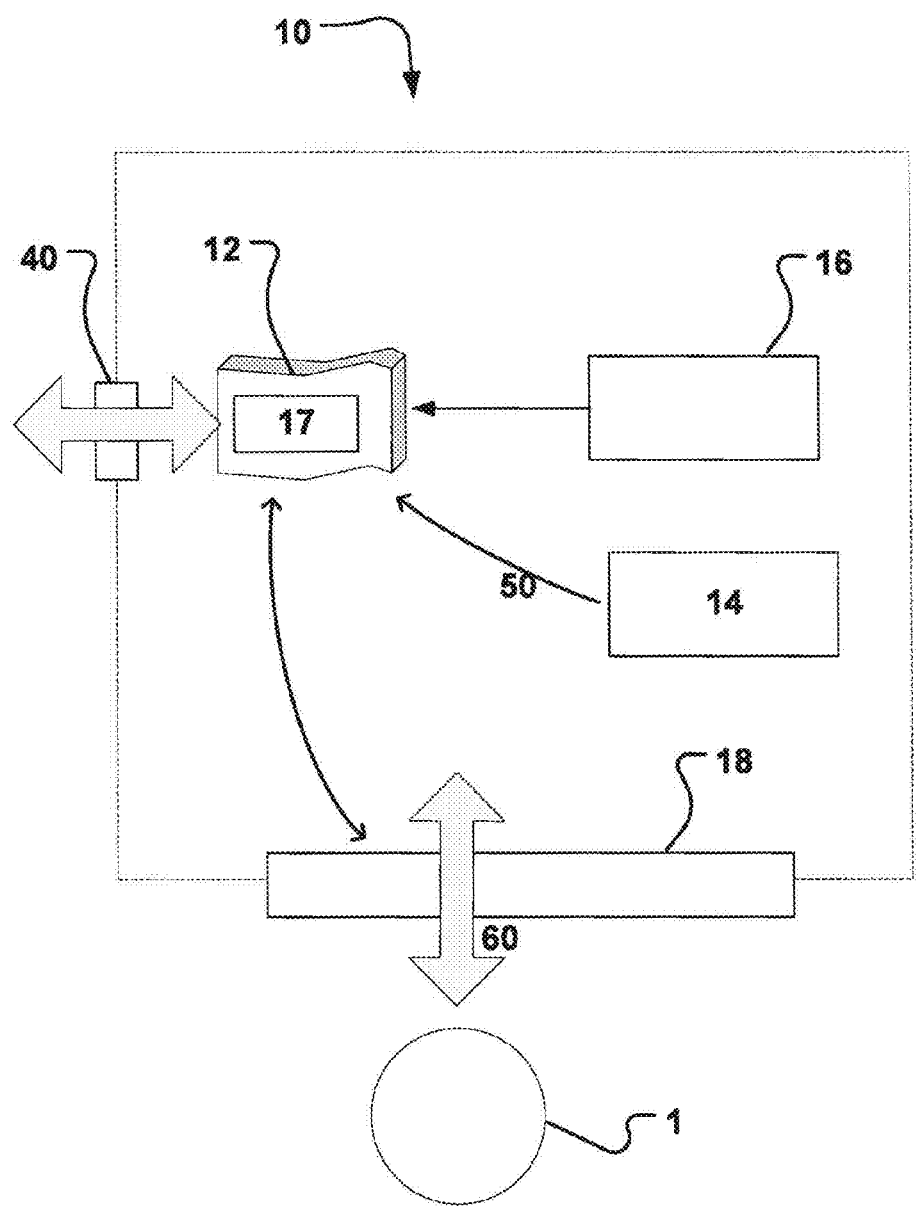
FIG. 1 is a schematic outline of an embodiment of a portable device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

As mentioned above, a patient may take notes between meetings with a physician. The notes are disclosed to the physician at such an occasion. However, the amount of papers with notes may get to be an overwhelming pile of documents for the physician to extract reliable information from, at least in the short time usually available for the meeting due to cost restrictions. The situation is most often intolerable for a physician in the health care system as the physician often have several patients in his care which all display similar amount of background information although highly individual.

According to embodiments of the invention, a dedicated handheld device is provided for managing occurrences and events in the form of a portable device 10. Thus, monitoring and managing of occurrences of a patient is facilitated. Measurements by an outpatient, e.g. at home, or another secure environment, are facilitated by the apparatus 10. Clinical personnel does not have to be present when using the device 10 for input of data.

In an embodiment illustrated in FIG. 1, an information flow of a portable device 10 is shown when handled by a user. The scheme illustrates a control module 12, a sensor module 14 and a user interface 18.

A provider, e.g. a physician in a medical department, has stored predefined data in the portable device 10. The stored data may comprise predefined instructions to be performed by the patient according to a specific or arbitrary schedule, as will be explained in more detail below. These instructions and the schedule are stored in a storage unit of the portable device 10, e.g. provided in the control module 12. The schedule may comprise fixed times, time intervals, or random timing of events. In accordance with these predefined settings, a user interface is activated to alert the user at the scheduled times. The patient's 1 response 60 is subsequently logged with a time identification in the information module in connection to the issued alert. Some alerts may invoke a sensor registration from the sensor unit 14 in those instances both the user's response 60 and corresponding sensor registration 50 are logged in the control unit 12. A more elaborate description of the involved modules is given below. In embodiments, the device does not comprise further elements that those described with reference to FIG. 1 and FIG. 2.

The portable apparatus 10 is adapted to manage a plurality of events related to a patient 1 and for recording and storing input data related to the events. The portable apparatus 10 comprises a man machine user interface 18. The man machine user interface 18 in turn comprises an input unit 30, such as buttons, for registering patient input data elements, and an output unit 38, such as a screen, display, and perhaps loudspeakers, for providing information elements to the patient. A schematic example is given in FIG. 2. The timer unit 16 is arranged to trigger at least a first event of the plurality of events and to tag the input data with a time stamp.

The input unit 30 is responsive to an invitation provided to the patient by the output unit and upon triggering the event, or being responsive to a patient self initiation.

The control unit 12 is arranged to provide the invitation as an instruction via the output unit to the patient to perform a motion exercise, upon the trigger from the timer unit or upon the patient self initiation.

At least one sensor unit 14 is arranged to record measurement data elements related to the motion exercise of the patient.

A storage unit 17 is arranged to retrievably store the input data comprising the patient input data elements and the measurement data elements, when recorded by means of the input unit 30 and/or the sensor unit 14, together with the time stamp, and wherein the storage unit is adapted to store the measurement data elements from the motion exercise performed upon the instruction or upon the patient self initiation of the motion exercise.

FIG. 2 is a schematic illustration of an implementation of the portable device 10. The embodiment of the portable device 10 comprises a dedicated hardware platform for long-term use over many years. The user interface is kept simple with few input buttons 32, 34, 36. There may be only a single input button, or two input buttons. A display 37 provides text output and graphics capabilities. The portable device 10 is battery powered. Instructions and input via the user interface 18 are kept simple, as will be described below.

The user interface may alternatively, or in addition comprise a tactile communication input and output interface. The user interface may alternatively, or in addition comprise an acoustic and/or visual output communication interface. The tactile communication interface may be adapted to provide a haptic feedback or a vibrational feedback to the patient.

In the illustrated embodiment, the user interface 18 comprises three buttons 32, 34, 36 for patient input. However, in other embodiments, the user interface may comprise even less buttons, such as two buttons for choosing between alternatives. In another embodiment, a single input button may be used to click through alternatives or values presented on the display. Alternatively, or in addition, a touch sensitive display with soft buttons may be provided. However, some patients have difficulties to press on a virtual button provided on a display. Therefore, physical present, dedicated buttons are preferred. The buttons are easy to identify, e.g. by color, tactile feeling, and/or size. Also, a clear tactile feedback, e.g. by a click or other haptic feedback, provides an increased user acceptance, in particular for elderly or motoric impaired patients.

In the illustrated embodiment, a pair of first buttons 32, 34 is arranged to choose between alternatives, e.g. by scrolling up and down with a first button 32 respectively a second button. The third button 36 may be used to confirm a chosen answer or other patient input. The third button 36 may be omitted by providing a specific graphical user interface on the display. In this case, a timer icon may be activated and displayed, wherein the input value is accepted after a desired or pre-defined confirmation time has elapsed.

The provided user interface is thus very simple, and is easily accepted by a patient without detailed training.

The sensor unit 14 may comprise one or more accelerometers. Accelerometric measurements are made simply by moving the portable device 10 itself during desired movements, as will be described in more detail below.

The portable device 10 is thus particularly suitable for use by elderly, or motorically disabled patients.

The portable device 10 is devised to manage two sets of different occurrences. The first aspect reflects a time induced occurrence while the second aspect reflects an event induced occurrence. The device is arranged to manage these two sets and to arrange them to a single set of occurrences where each occurrence is tagged with a time mark. When the recorded information is downloaded from the portable device to a work station at a local health provider, medical department, health clinic or surveillance site, the stored information data is arranged to be analyzed in one data batch. Data transfer is provided via an interface 40.

The first set of occurrences, namely the time induced occurrences, is predefined by the health provider, medical department, health clinic or surveillance site. The predefined information is for instance arranged at a work station and transferred to the portable apparatus at the provider to reflect the needs or occurrences which the provider regards as essential to be conducted in order to get a reliable result of the surveillance performed. By defining the events in time and their repetition interval, a complex schedule is set forth. These time induced events comprise for instance one or more requests or questions to the user which will emerge on the portable device at the prescribed time and intervals.

These questions could either be answered by a discrete value Yes/No or be rated on a scale.

Typical request questions are e.g.:
Do you feel sick?
Have you slept well?
Have you taken you medication?
Did you tumble?

The user answers each of these single questions by pressing an appropriate answer button 32, 34 which is related to a text or graphical value on display 37 adjacent the button 32 respectively 34. The portable apparatus will record the question and answer given together with a time stamp from timer unit 16 in storage unit 17 when it was entered into the device. In absence of an answer input by the user, this is also stored as a data element in storage unit 17.

Other types of question is where the patient is demanded to rate his/hers experience on a scale, e.g. from 0 to 10, or 1-10, or 1-5, etc., in some individual arbitrary index scale, or as predefined categorized answers. The later ones may be orderly organized in a predefined manner.

Categorized answers are pre-defined multiple answers or input choices that are presented to the patient. Such multiple choice answers may for instance be: 0—over agile, 1—normal/on, 2—stiff/off.

A few, e.g. three, pre-defined alternative reply options provides improved quality of measurement data. In case the patient has too many alternatives, the reply otherwise may be objectively wrong or not entered by the patient as it may be too complicated to choose a correct input. It is for instance difficult to grade pain on a scale from 1 (little) to 10 (heavy).

The index maybe based on the individual such that no interference occurs with other individuals, and fluctuations in the rating may in embodiments be normalized to an individual patient. This could reveal that the patient scores for the same question differently in the morning than in the afternoon, despite that e.g. medication was taken with the same interval prior to the particular question. A scoring question may also be used to enter a specific amount, e.g. a number of tablets taken to evaluate a dosage of medication taken by the patient.

Typical scoring questions are e.g.:
How exhausted are you?
How much did you hurt yourself?
How many tablets did you take?

In case of absence of inputs from the user this may be stored as input information or data element itself. This absence may be valuable for a later diagnosis. As mentioned afore, occurrences where the user is not answering the displayed question or request are stored and may provide valuable information to the diagnosing physician when the stored data later is available to the latter. If these occurrences of no-answers are frequent and perhaps even showing some pattern in respect to the non-answered questions or time of the day of no-answer, it may carry essential information to the physician or surveillance site to investigate this pattern further. This information was hitherto not easily detected, due to the current procedure of note taking. Either the patient did not remember the occurrence, the patient was not at all aware of it, or had forgotten to take a note.

In case of absence of inputs from the user this may trigger a reminder a pre-defined number of times. The reminder may be set to ask the patient an unanswered question again, or to make a measurement or a measurement exercise.

More elaborate and complex question structures may also be provided by the portable device 10. An example for a more complex structure is a tree of related questions and answers or events. An example is given below:

"Please enter your current movement capability:
0—over agile, 1—normal/on, 2—stiff/off"

The user input is stored together with a time stamp, as described above.

Depending on which input the user makes, a subsequent question or event is presented, e.g.:

Input "0": Please grade your over agility from 1 (little) to 5 (much)
Input "2": Please grade your over agility from 1 (little) to 5 (much); a subsequent question may for a range of higher inputs (very stiff) be:
Do you have a spasm Yes/No
If Yes: Grade your spasm from 1 (little) to 5 (intense)

It may also be predefined to invite the patient to make a measurement, e.g. based on the accelerometer in the apparatus.

The second set of occurrences is induced by the user. At such events, the user activates the portable apparatus and chooses one of the predefined questions or event descriptions which most accurately reflects the occurrence experienced by the user. Although the question or event description is predefined by the provider, the user activates it and logs an answer into the portable apparatus 10 in-between predefined time slots. The event will be recorded with the chosen question or event description, together with the given answer or scaling and with a time stamp when it was entered into the device. Examples of such questions are for instance some of the previous single or batch questions or a specially defined event description reflecting an event which may occur intermittent more or less often.

The portable device 10 may be updated with new, specific questions or event descriptions, in dependency of the need of the individual patient.

Typical special event descriptions are e.g.:
I am dizzy.
I have headache.

Several single questions may be batched together compiling a complex structure. Depending on a first answer, a second question may be chosen in an appropriate way. For instance, depending if the answer on the first question is yes or no, a different question is displayed for answering by the user.

Typical sequences of questions and answers are e.g.
Did you tumble?—Yes
Did you hurt yourself?—Yes
How much?—Enter from 1 (little)—5 (very much)
END
I have headache.
How much?—Enter from 1 (little)—5 (very much)
Did you take a medicine? Yes/No
If Yes: How many tablets? 1-10
END Presentation of questions are controlled by control unit 12. The answers or other input entered by the user are stored in the storage unit 17 of the portable apparatus 10. This data is available for later analysis.

Analysis of the data is made externally to the handheld device 10. The handheld device 10 is thus kept with few components and less frequent updates. Analysis may be provided on an external workstation, when the data is uploaded from the portable apparatus 10 to the workstation. The workstation may be a medical workstation available for preparing the collected data for access to the physician. The interface 40 may be a communication unit that comprises a communication link by wire, e.g. USB (Universal Serial Bus) or Firewire (I1394) transmission. The communication unit may in addition or alternatively comprise a wireless communication link, e.g. bluetooth or infra red transmission.

An embodiment of a system comprises in combination at least one of the portable devices or apparatus 10 and an external processing unit. The storage unit 17 is arranged to provide the stored input data for processing to the external processing unit, wherein the external processing unit and/or the control unit is adapted to derive diagnostic data from the stored measurement data elements. The external processing unit and/or the control unit is adapted to provide a long-term summarized report of the stored input data for a physician.

The external processing unit may be a local work station adapted to be managed by a healthcare provider. The local work station is arranged to provide at least one portable apparatus with information and ordination requirements. Further, the local work station is arranged to analyze transmitted information from the at least one portable apparatus.

Alternatively, in some embodiments, the analysis of data may be performed in the device 10.

Typical Reports

The data stored in storage unit may provide trends, daytime curves, relations between questions and answers, comparison with other patients or a population, comparison with the patient over time, e.g. before and after taking medicines, or in a long-term trend over days, weeks, months or years, etc.

In particular for PD patients, roughly 70% of the PD patients suffer from undesired motoric movements to some degree, from severe to mild. As such, a surveillance of the progression of the disease may not comprehensively be based on this parameter for all patients. However, applicants have realized that all PD patients suffer from a change of muscle tonus and especially muscle relaxation. The change in muscle tonus is individual due to the progression of the disease and also reflects the level of medication. The medication may affect the patient differently depending on various parameters, such as food intake, physical activity, other medicine taken, too high dose of medicine taken, too low dose of medicine taken, etc. With an insufficient prescription undesired movements are not reduced or eliminated. If the amount prescribed medication is more than advisable at the given occasion the patient commonly is affected as the patients movements are either uncontrollable and/or when attempting to make an arbitrary movement the actual movements are overshooting the desired anticipated movement due to a lack of motoric control (over-agility). Both these scenarios commonly occur in various degrees (ON-OFF, see below) for a PD patient because of the disease's inherent variability.

By investigating and monitoring the long term trend an objective estimation of the progression is feasible, for the short term perspective the experienced momentary muscle tonus reflects among others the level of medication needed in respect to a measured result. With these sets of measurements, the physician responsible for the patient has to judge and then to prescribe medication which yields the PD patient a better quality of life both in short term and long term perspective.

In more detail, medication for PD usually causes the symptoms of PD patients to go away for hours at a time (ON times), then return (OFF times). During ON times, PD patients report they feel relatively fluid, clear, and in control of their movements. During OFF times, PD patients experience PD symptoms, including stiffness, lack of muscular coordination, or pain.

Patients usually cycle between ON and OFF periods several times during a day. In case the patient takes a too large dose of medicine, the patient may get over agile. When the patient takes a too low dose of medicine, or when the medicine is washed out, the patient stays in or returns to the OFF state.

For PD patients, the band in which the patient is in the ON state narrows over time as the disease develops. This narrowing mostly develops over a couple of years, and makes a correct medication increasingly difficult, both with regard to dosage and timing of administration. The present device or apparatus 10 facilitates to fine tune dosage and timing of administration.

The portable apparatus 10 facilitates to provide long-term measurements concerning OFF times. OFF times are identified from the accelerometer measurement curves. The accelerometer measurement curves also facilitate to identify that an OFF time is approaching. Parameters identified from the accelerometer measurement curves include a slowing down of exercises performed, due to increasing muscle stiffness.

There is a desire of PD patients to arrange their daily life around ON and OFF periods. Thanks to the information and reports provideable by using the portable apparatus 10, the doctors of the PD patients can learn to adjust medication efficiently with regard to increasing the portion or time duration of ON periods. The collected information may also facilitate planning of the ON periods in a daily rhythm. Thanks to this fact, the PD patients using a portable apparatus 10 may lead a closer to normal life for a longer period during their disease.

In an embodiment, at least one accelerometer is integrated in the disclosed device 10 as a sensor for monitoring and surveillance of the muscle tonus of the patient. In an embodiment, the at least one accelerometer is adapted to measure a motion of a body portion of the patient while the portable device 10 is in a fixed relation to the body portion during the exercise. In this manner the measurement data is related to a registered movement of the portable device 10 in at least two dimensions during the motion exercise. The accelerometer is preferably a three-axis accelerometer, measuring acceleration in three dimensions.

The portable device 10 is adapted to serve as a mass m to be moved by the patient during the exercise, wherein the apparatus is adapted to be held or attached to the patient during the exercise.

The portable device 10 may be used to ask the patient to make certain exercises (via the user interface), which exercises then are registered by means of the accelerometer. The data provided by the accelerometer is stored in the memory 17 of the portable device 10, related to the exercise made, and the time at which it was made.

Several potential movements can be obeyed in the exercises to follow the progression of the disease.

As the population of PD patients are rather heterogenic and the result must be easy to examine for the health provider, the potential movements to perform are limited to certain well repetitable exercises.

The motion exercise is adapted to provide a degree of muscle tone or muscle relaxation of the patient. The accelerometer of the apparatus 10 is adapted to provide the measurement data for the degree of muscle tone or muscle relaxation.

FIGS. 4A-C, 5A-C, and 6A-C are graphs of measurement curves made by means of the portable device.

Figure 4A:
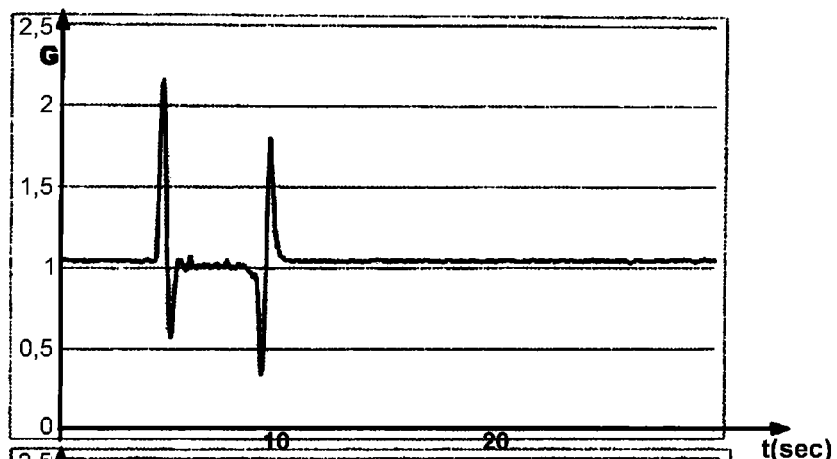
Figure 4B:
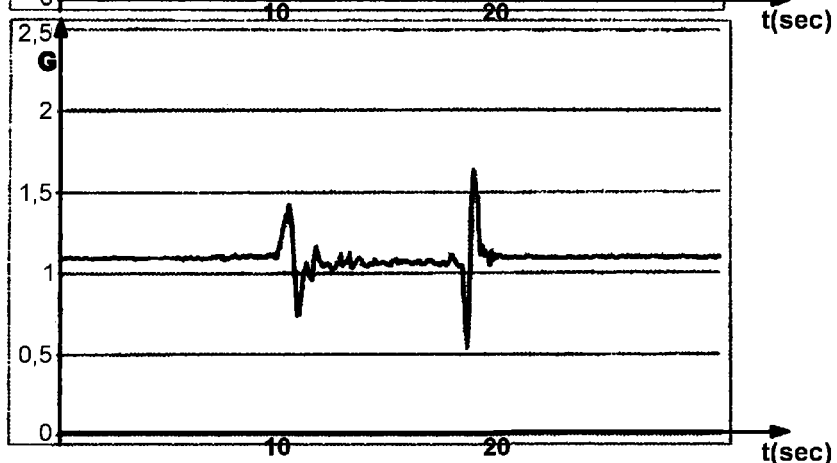
Figure 4C:
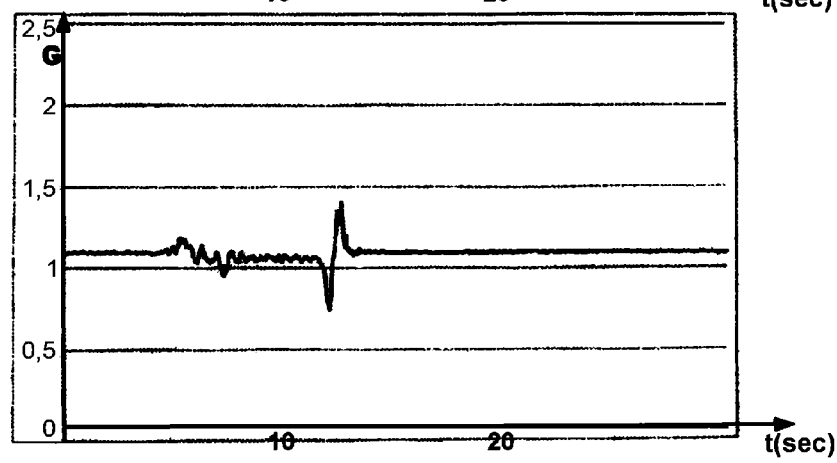

The FIGS. 4A, B, C show recordings of such movements with the arm straight towards the floor holding the device 10, by raising the arm straight out from the body in the frontal plane, perpendicular to the sagittal plane, and holding the device for a couple of seconds. And finally the hand holding device 10 is dropped in free fall. Free fall is a desirably rapid motion of lowering the arm to approximately the same position from which the exercise started. The latter will show for a healthy individual a recording near free fall, zero gravity, while patients suffering from PD have difficulties to reach this level of free fall, depending on their ON/OFF status and muscle tonus. Thus, the accelerometric measurement gives a recorded measurement for the state of PD at the time of measurement.

Parameters, which values are determined from or by these measurements, include for instance amplitude, maximum, minimum, mean or average value, statistical values like standard deviation, width of peaks or pulses, frequency of movements, and arbitrary combinations thereof. A comparison of the measured values with previously measured values of a healthy standard population provides for a diagnoses. For instance PD patients typically show deviating values, such as smaller movement amplitudes, slower movement frequency, more jagged, or jerky motion, in relation to a healthy population.

Alternatively, or in addition, pause times in movements may be analyzed. For instance, certain PD patients perform movements within narrow tolerances like healthy persons—however, with pause times introduced into the movements. Smooth movements of healthy persons thus become chopped, or jerky, with motion pauses (stagnation, standstill) during adjacent phases of the total movement. Thus, the total time for a movement from start to stop becomes longer for these PD patients, but the time when in motion is similar to that of healthy persons. Thus, diagnosis may be based on these pause times. One measure is the accumulated pause time. Another measure are individual pause times within a motion. The longer the pause times, or accumulated pause times, the larger the deviation from a healthy population.

When having an accelerometer in the handheld device 10, a measurement value may be determined as a vector r from the square root of the sum of $(X^2+Y^2+Z^2)$m wherein X, Y and Z are values obtained from the three axis of the accelerometer. Other values are velocity and position of the device 10, as described below.

Between individual PD patients enormous differences exist in the pathological picture. An abundance of different medicines make individual medication difficult for the clinicians. However, there is a need for an individual medication plan for each patient.

The measurement values of the parameters provide for an individual analysis of PD patients. This is in particular true to identify and adjust a daily rhythm of a patient; to adjust medication to this rhythm; identify long-term effects of medication, identify long-term changes in the pathological picture and adjustment of administration and/or type of medicine; etc.

During the exercises, the handheld device is held by the patient for registration of arm movements. It may also be put into a sock for registration of leg movements.

The user interface 18 may provide an indication to the patient during the exercise for a control of a progress of the exercise, or to indicate borders between different stages of the exercise, including sounds, spoken words, beeps. This indication may be based on the knowledge of the apparatus 10 in space relative a starting point, as is described below.

Other exercises can for patient with limited residual movement capability be less demanding exercises such as having to turn a string or small rope around the device 10. This exercise occupies both hands of the patient; one holding the string and the other holding the device while the string is wound up on to the device.

Still other movements for investigation comprise large displacements patterns, such as moving the activated device 10 from a table in front of the patient to a location some distance away. This could include rising from the chair grabbing the device, taking a shorter distance walk, e.g. two to four steps, and finally to place the device on the desired position.

Still further movements are possible, such as described hereinafter.

A first category of movements comprises coordinated motions in space. These motions include for instance (1) throwing the portable apparatus 10 upwards without releasing grip and then lowering it softly back to the starting point of the exercise in free fall. Alternatively, the movement may comprise (2) throwing the portable apparatus 10 upwards while releasing grip and then catching the portable apparatus on return in free fall.

Here, the measurement data provides data for assessing vertical muscle relaxation of the patient. For a healthy person, the free fall phase results in a weightless ballistic curve, i.e. a g-force ("G") of approximately zero is measured. For a motorically impaired patient, a measurement value larger than zero G will be measured during the free fall phase. The current value for one G may be calibrated into the portable apparatus when it is at rest. The current value for zero G may be calibrated into the portable apparatus when it is identified being in the above mentioned free fall phase.

For these exercises G a healthy person accelerates the device 10 from 1 G to approx. 2.3 G in dependence of the capability of ease of motion activation (parameter provided by measurement) of the patient. Then a gravity free return of approx. 0 G under less than 1 second follows (providing a measure for muscle relaxation).

For exercise (1) subsequently, a negative acceleration (deceleration) of approx. 3 G follows before returning to rest at 1 G.

For exercise (2) the device 10 is caught in the hand under detension to approx. 0.4 G.

A second category of movements comprises movement of at least one hand of the patient in a controlled, pre-defined motion. Such motion comprises for instance (3) winding a thread around the portable apparatus. Alternatively, the portable apparatus may be (4) moved back and forth horizontally on a sturdy surface. In this case a measure independent of vertical relaxation is provided. Alternatively, the patient may (5) imitate a whipping motion. These movements are to be performed with >1 turn per second under a predetermined time of e.g. 10 seconds. For a healthy person, maximum values of measured acceleration are around 2.4 G and minima around 0.2 G. The time between changes of muscle activation and relaxation. From these measurements, the muscle tonus, rigidity or hypotonic may be quantitatively determined by comparisons with measurements performed by a healthy population.

A third category of movements comprises movements of an extremity.

Figure 5A:
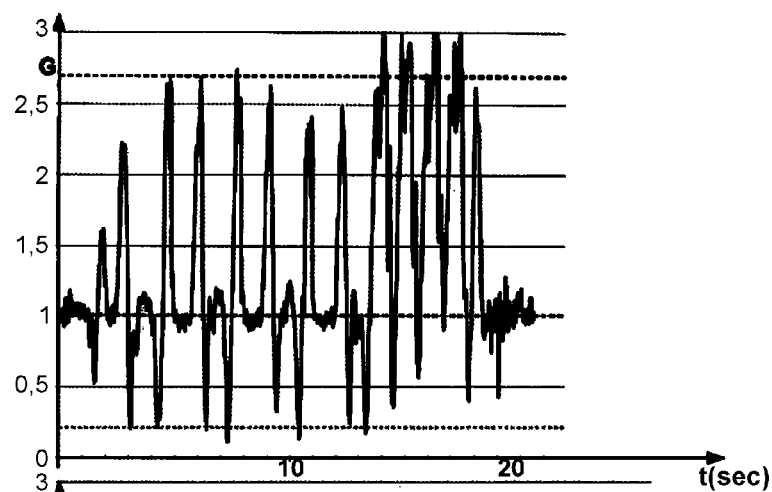
Figure 5B:
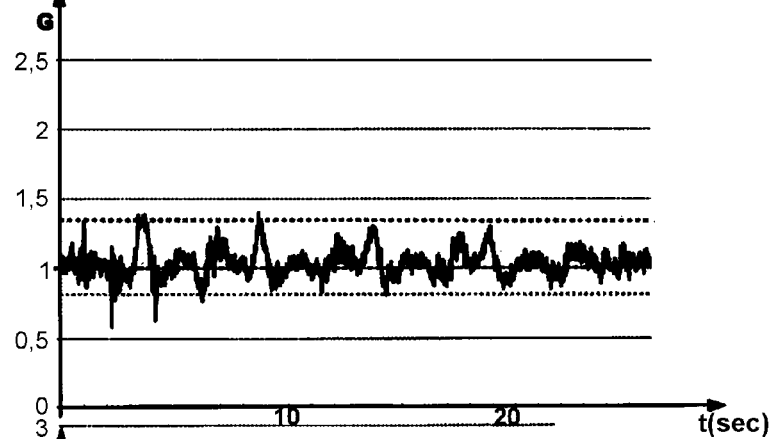
Figure 5C:
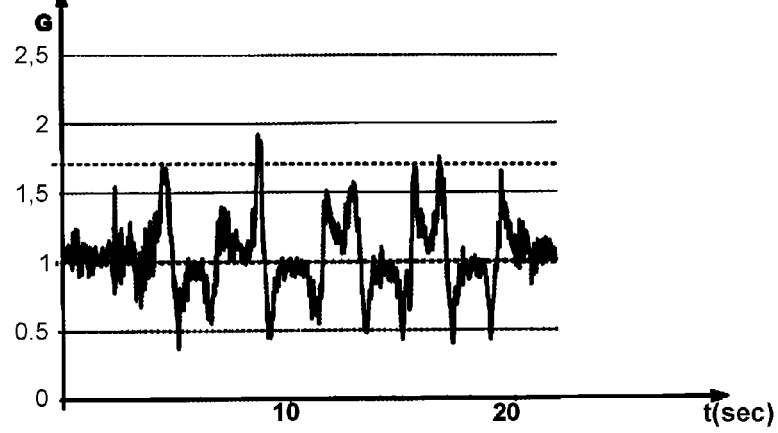

Such movements comprise for instance repetitively lifting an arm or leg, such as lifting an arm quickly upward for instance up to approximately eyelevel, staying in that position for a predetermined time, and then lowering the arm, and repeating the exercise a number of times. An example of such measurements is shown in FIGS. 5A-5C for a healthy person (FIG. 5A), a PD patient in an OFF state (FIG. 5B) and an ON state (FIG. 5C).

For a healthy person, the lifting motion has a initial average acceleration maximum of approx. 2.6 G followed by a minimum of 0.2 G before a rest at 1 G. The lowering of the arm with gravitation results in a downward acceleration to a minimum at approx. 0.2 G average acceleration minimum; before the lifting muscle decelerates at approx. 2.6 G average maximum acceleration and a return to 1 G.

From these measurements, the muscle tonus, the tardiness or stiffness of PD patients may be quantitatively determined by comparisons with measurements performed by a healthy population. A PD patient in an OFF state (FIG. 5B) has significantly longer times between repetitive movements, as well as significantly lower average maximum acceleration (in the example 1.4 G) and average minimum acceleration (in the example 0.8 G). The same PD patient in the ON state (FIG. 5C) has increased lower average maximum acceleration (in the example 1.7 G) and average minimum acceleration (in the example 0.5 G).

Alternatively, an arm may be moved in a circular motion.

A fourth category of movements comprises displacement of the patient by walking. For such movements, the portable apparatus 10 may be inserted into a sock worn by the patient during the motion exercise. An example of such measurements is shown in FIGS. 6A-6C for a healthy person (FIG. 6A), a PD patient in an OFF state (FIG. 6B) and an ON state (FIG. 6C). The movement is to be performed as normal walking a couple of meters, back and forth, as well as with normal arm movement.

For a healthy person (FIG. 6A), top accelerations of approx. 3 G are measured. These occur when the heel meets ground, followed of a phase of 1 G during the support phase, and subsequently an acceleration of approx. 2 G at forward movement followed by lowering of the foot towards ground level under muscle relaxation and an average minimum acceleration of approx. 0.6 G.

From these measurements, the muscle tonus, the tardiness or stiffness of PD patients may be quantitatively determined by comparisons with measurements performed by a healthy population. A PD patient in an OFF state (FIG. 6B), in contrast, will not top more than an average maximum acceleration of approx. 1.5 G. and a step rate that is lower than that of a healthy person. A PD patient in the ON state (FIG. 6C) has re-gained pace rate as well as average maximum acceleration of approx. 2.3 G.

A fifth category of movements comprises repetitively raising and seating down of the patient. A maximum acceleration is measured at sit-down during an ongoing deceleration. A further acceleration maximum of approx. 2 G during a co-ordinated forward-upward movement. The latter movement is fragmented into two acceleration maxima for PD patients.

Detectable and examinable movements are not limited to the above disclosed. The portable device 10 is preferably capable of registration of any arbitrary spatial movement within the 3D-space.

The measurement data provides a measure for quantitative neurology. States of neurological diseases may thus conveniently be quantitatively determined from the measurement data. Quality and plausibility of patient information entered may be improved based on this measure, as described above.

A portable apparatus may alternatively or in addition measure g-forces continuously and ask pre-defined questions depending on measurement values. For instance, when peak accelerations occur, which indicate that the patient may have tumbled, the apparatus may ask the patient to confirm this tumbling via the user interface for storage in the storage unit. Without user confirmation, no event is stored.

The portable apparatus 10 may also be used for registration of movements simulating handwriting. Thus, handwriting is detected by accelerometric measurement. Handwriting is largely dependable on muscle tonus and may thus be used for detecting a degree of PD in accordance with the above description.

The portable apparatus takes in an embodiment form of a pen. Alternatively, or in addition, a pen may comprise an accelerometer and transmit measurement data of handwriting to a portable apparatus 10 for storage. Alternatively, or in addition, the pen may comprise another handwriting registration unit, like an optical reader as known from Anoto® pens.

FIG. 3 is a flow chart of an embodiment of a method 300 implemented by means of the portable device 10.

The method is a method of diagnosing a degree of a neurological disease or an effect of a medication on said neurological disease. The method 300 comprises registering 310 movement of said portable apparatus 10 by registration of an output signal from an accelerometer of the portable apparatus during a pre-defined motion exercise, and storing 320 said output signal as measurement data elements, and analyzing 330 said measurement data for determining said degree of a neurological disease or an effect of a medication on said neurological disease.

The method further comprises comparing 340 values of parameters analyzed from said measurement data with corresponding values from a standard population for said diagnosis.

The measurement is repeated at fixed or arbitrary time intervals or upon user initiation, and wherein a long-term relation determined at step 350 from a plurality of said measurement data elements is used for adapting 360 a dose and time of administration of said medication for improving said effect thereof. A measurement value is this provided for an effect of a medication on a disease, e.g. on a neurological disease, such as Parkinson's Disease. An adjustment of an active dose and/or time of administration of such a medication may thus be done based on the measurement value.

In an embodiment said patient is a PD patient, and wherein said apparatus is used to provide input data with regard to ON-OFF periods of said patient.

The measurement values may be used as values in a motor section of an Unified Parkinson's Disease Rating Scale (UPDRS), which is a rating tool to follow the longitudinal course of PD.

The method comprises prediction of an OFF period from said user input in an embodiment.

The method may comprise transmitting a questionnaire via a communication link to said portable apparatus from an application on a local computer system, and wherein said questionnaire comprises an instruction to initiate said motion exercise.

The questions of said questionnaire may be correlated to measurement values registered from said motion exercise.

The method may further comprise performing a plausibility control by comparing said measurement values with answers of a patient to at least one well-being question.

In an embodiment, a computer program is provided enabling carrying out of embodiments of the aforementioned method.

The aforementioned method may be implemented in form of a system having suitable units for performing the method.

As mentioned above, by way of measuring a value acceleration and time of the acceleration, a change of position may be calculated. Thanks to an accelerometer providing accelerometric measurement values in three dimensions, this may be provided in three dimensional space.

Thanks to a three axle accelerometer and a timer unit in the portable apparatus 10 for managing a plurality of events related to a patient 1, the speed and direction of a movement of the apparatus 10 between two measurement points is determinable. Thanks to a sampling rate, of e.g. 100 Hz, it is suitably calculated which distance and in which direction the apparatus 10 has been moved between two measurement points (samples).

In this manner, a current position in space and path of travel and a distance thereof may be determined relative to a starting point in space.

This may be based on the following:

Acceleration a is measured in m/s2. By multiplying a measured acceleration a by the determined time t during which the acceleration is measured (e.g. sample time or accumulated sample times), the resulting rate of speed or velocity v is determined in m/s. Multiplying the velocity v once more by the time t, the travelled distance d is determined in meters. This can be split up in three dimensions, related to each of the three axis of the three dimensional accelerometer: x, y, z. Thus the position of the device 10 is known in three dimensions X, Y, Z relative to the starting point: $Z=az \times dz$; $Y=ay \times dy$; $X=ax \times dx$. Alternatively, a vector r and an angular value $\partial$ in space may be determined in relation to the starting point, e.g. by $r=sqrt(x2+y2+z2)$, and $\partial x=\cos^{-1}(x/r)$ $\partial y=\cos^{-1}(y/r)$ $\partial z=\cos^{-1}(z/r)$.

Another parameter that is determinable is the force F, which acts upon the device. As the weight m of the device is known, the Force is determined by $F=a \times m$. The Force F may be a basis or parameter for diagnosis of neurological diseases as described above.

Having at least one such accelerometer in device 10, this provides for further detailed data concerning a motion during a defined exercise of a patient. A kinematic determination of a three dimensional motion pattern is provided. From the detailed data, it may be determined if such a motion exercise has been correctly performed. Alternatively, or in addition, a training of a user of the device 10 may be based on the detailed data. For instance, when a user is outside of certain tolerances, training may be controlled by instructions given by the device 10 to optimize the motion exercise. Instructions may be given as audio instructions, audio feedback, or haptic feedback.

The motion pattern in space may be stored.

The motion pattern may be compared to that of a healthy population and a diagnosis may be provided based on this comparison.

The motion pattern may be checked if it correlates and/or to which degree it corresponds to pre-determined motion patterns, e.g. based on previous measurements. A comparison of a motion pattern performed by a user of the device 10 is thus provided with a template motion pattern (i.e. a "correct" motion pattern). The comparison may be done to see if deviations exist within a maximum tolerance in order to determine if the motion pattern has been correctly performed by the user of device 10.

The motion pattern differs between individual patients. Differences in motion patterns are for instance based on age of the patient, a type of disease from which the patient suffers, medication of the patient, etc. Thus these factors influencing the motion pattern may be diagnosed. Diagnosis may be based on the above determined deviation.

In a particular case, the physical age of the patient may be determined in this manner. Younger persons have for instance a more direct motion pattern in certain motion exercises. For instance when raising from a sitting position and moving towards a target, persons of higher age tend to divide the motion pattern into two sections of raising up and subsequent moving towards the target. Younger persons tend to move towards the target already when moving. The physical age may differ from the actual age of the patient and thus be determined.

A further neurological disease that may take advantages of the present device and/or method is Stroke. Stroke patient most often are affected on one half of the body only, due to a blood clot affecting only one hemisphere of the brain. In this manner, there is a motorically better functioning half of the body than the other half. For instance one arm may perform healthy movements, while the other arm has reduced agility. In this manner, the patient may perform motion exercises with both arms. The healthy arm serves as a reference. The impacted arm is used for measuring the degree of disease, the effect of medication, and for training—based on the device 10 and corresponding methods described above.

A further treatment area that may take advantages of the present device 10 is orthopedic diseases. A reduced agility of joints or limbs may be quantified. A motion pattern may be advantageously controlled. Effects of medication may be followed-up. Improvements of a range of movement can be trained and measured.

Fine motor ability may be trained by the device 10. For instance a ball may be simulated on the target that shall be brought into a target. By holding the device 10 in the hand and measuring tilting of the device based on the accelerometer measurements, a graphic simulation of the ball may be moved accordingly with respect to hand movements.

EXAMPLE

Figure 7:
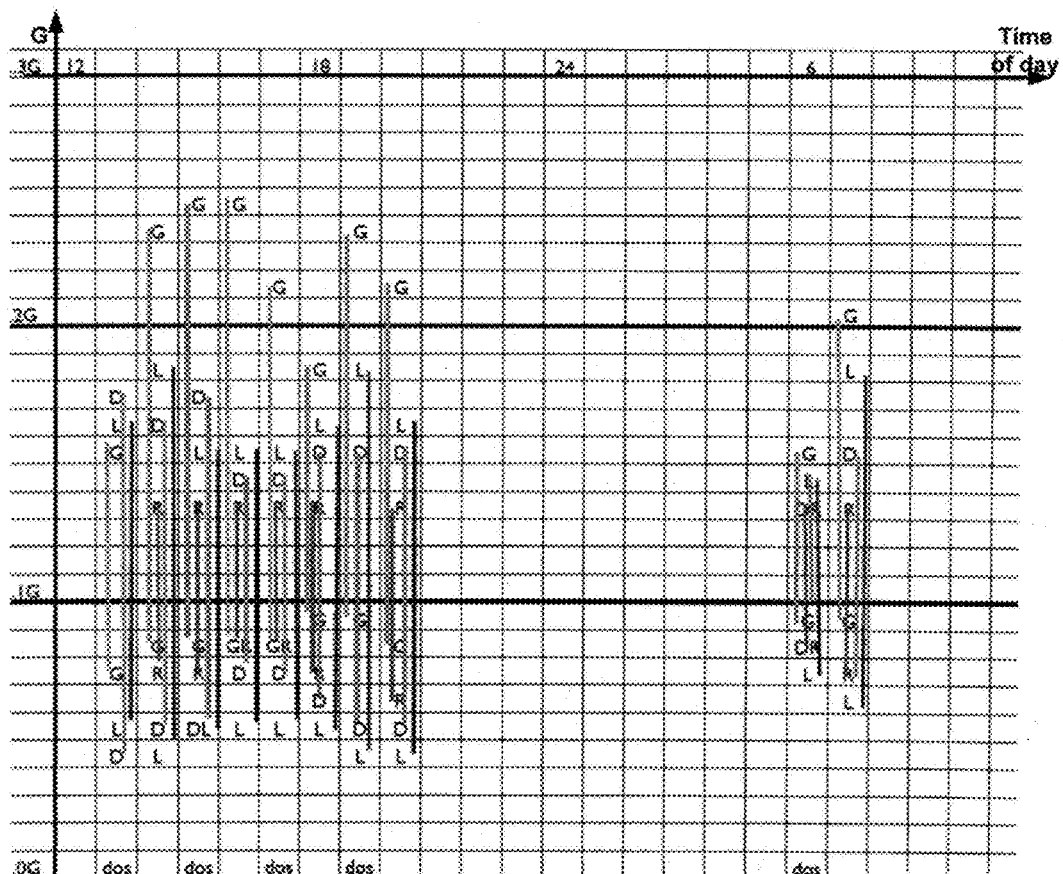
FIG. 7 is a graph illustrating a series of amplitudes of accelerometer measurements of a patient over a time period.

FIG. 7 is a graph illustrating a series of amplitudes of accelerometer measurements of a patient over a time period. The graph is an example of the aforementioned reports.

The patient was a 80 year old PD patient.

Various motion exercises were performed every hour and stored in a handheld device 10. The exercises, abbreviated in FIG. 7, are denoted with G (walking), R (raising), D (screwdriver imitating motion), L (lifting device).

As can be seen in FIG. 7, the patient was very immobile or stiff in the morning. This is identified by a small amplitude and a comparatively large minimum acceleration (lack of muscle relaxation). After dosage of medication (shown at "dos" in FIG. 7), a clear improvement can be seen with increased amplitude and lower minimum acceleration (improved muscle relaxation thanks to the administered drug).

A possible diagnosis is in this example that the patient needs an additional administration of medication during the night. In this manner the mobility of the patient would be improved in the morning.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A portable apparatus to manage a plurality of events related to a patient and to record and store input data related to said events, said portable apparatus comprising: a user interface comprising an input unit configured to register patient input data elements and an output unit configured to provide information elements to said patient; a timer unit arranged to trigger at least a first event of said plurality of events and to tag said input data with a time stamp; a control unit, arranged to provide an invitation as an instruction via said output unit to said patient to perform a desired movement in a motion exercise, upon said trigger from said timer unit or upon a patient self-initiation; at least one sensor unit arranged to record measurement data elements related to said motion exercise of said patient, wherein said at least one sensor unit comprises at least one accelerometer adapted to measure a motion of said portable apparatus; and a storage unit, arranged to retrievably store said input data comprising said patient input data elements and said measurement data elements, when recorded by said input unit and/or said sensor unit, together with said time stamp, and wherein said storage unit is adapted to store said measurement data elements from said motion exercise performed upon said instruction or upon said patient self-initiation of said motion exercise wherein: said input unit is responsive to said invitation provided to said patient by said output unit and upon triggering said event, or to a patient self-initiation; said portable apparatus is adapted to be held by said patient, or attached in a fixed relation to a body portion of said patient, and thus to serve as a mass to be moved in a desired manner by said patient during said motion exercise in such a manner that said measurement data elements are provided that are related to a movement of said portable apparatus in at least two dimensions by said patient during said motion exercise; and said control unit is a unit configured to correlate said instructions to said measurement data elements and to analyze said measurement data elements to determine a degree of a chronic disease, wherein said analyzing unit is adapted to calculate a speed, direction of movement, distance, time and force that acts upon the device from said measurement data elements and said time stamp stored together, as provided by said movement and said mass of said portable apparatus, and whereby said control unit is adapted to provide a determination that said movement of said motion exercise has been correctly performed.

2. The apparatus according to claim 1, wherein said motion exercise is adapted to provide a degree of muscle tone or muscle relaxation of said patient based on said measurement data, and wherein said accelerometer is adapted to provide said measurement data for determination of said degree of muscle tone or muscle relaxation.

3. The apparatus according to claim 1, wherein said accelerometer is adapted to provide a kinematic determination of a three dimensional motion pattern during said motion exercise.

4. The apparatus according to claim 1, wherein said motion exercise is selected from a variety of motion exercises comprising:
 a) coordinated motions in space;
 b) movement of at least one hand of the patient;
 c) movements of an extremity;
 d) walking;
 e) repetitively raising and seating down; and/or
 f) simulating of free fall.

5. The apparatus according to claim 1, wherein said user interface has a tactile communication input and output interface, and an acoustic and/or visual output communication interface, and wherein said user interface is adapted to provide an indication to said patient during said exercise for a control of a progress of said exercise, or to indicate borders between different stages of said exercise, including sounds, spoken words, and/or beeps.

6. The apparatus according to claim 5, wherein said tactile communication interface is adapted to provide a haptic feedback or a vibrational feedback to said patient for said control of progress.

7. The apparatus according to claim 1, wherein said patient input data and said measurement data are related, and wherein said storage unit is adapted to, in an absence of input data, to register and store a no input data element together with said time stamp.

8. The apparatus according to claim 1, wherein said events are triggered at predefined scheduled times or at arbitrary times.

9. The apparatus according to claim 8 wherein said predefined schedule settings comprises information and ordination requirements defined by a healthcare provider.

10. The apparatus according to claim 1, wherein said apparatus comprises a communication unit, and wherein said sensor unit is adapted to communicate with an external sensor device via said communication unit.

11. The apparatus according to claim 10 wherein said communication unit is adapted to transmit information and ordination requirements defined by a healthcare provider.

12. The apparatus according to claim 1, said storage unit comprising a memory unit configured to store an information data base for predefined scheduled settings; and wherein said information data base comprises a plurality of questions.

13. A system comprising in combination at least one apparatus according to claim 1 and an external processing unit, wherein said storage unit is arranged to provide said stored input data to process to said external processing unit, wherein said external processing unit and/or said control unit is adapted to derive diagnostic data from said stored measurement data elements; and wherein said external processing unit and/or said control unit is adapted to provide a long-term summarized report of said stored input data for a physician.

14. The system of claim 13, wherein said external processing unit is a local work station adapted to be managed by a healthcare provider; wherein said local work station is arranged to provide at least one portable apparatus with information and ordination requirements; and wherein said local work station is arranged to analyze transmitted information from said at least one portable apparatus.

15. The system of claim 13, wherein said patient is a patient suffering from a neurological disease, Parkinson's disease, and/or pain.

16. The system of claim 15, wherein said sensor unit comprises an accelerometer, and said diagnostic data is related to Parkinson's disease and based on a degree of muscle tone derived from said measurement data.

17. The system of claim 13 and further comprising: a unit configured to register movement of said portable apparatus by registration of an output signal from an accelerometer of said portable apparatus during a pre-defined motion exercise, and to store said output signal as measurement data elements, and a unit configured to analyze said measurement data to determine a degree of a neurological disease or an effect of a medication on said neurological disease.

18. The system of claim 17, wherein said unit is configured to analyze said measurement data is adapted to analyze pause times in said movements, and wherein said diagnosis is based on said pause times.

19. The apparatus according to claim 10 wherein said external sensor is selected from the group consisting of a further accelerometer, a blood pressure monitor, and a watch-type physiological sensor.

* * * * *